(12) United States Patent
Monroe et al.

(10) Patent No.: US 6,790,221 B2
(45) Date of Patent: Sep. 14, 2004

(54) CATHETER TIP DESIGNS AND METHOD OF MANUFACTURE

(75) Inventors: Lance A. Monroe, New Hope, MN (US); Andrew D. Bicek, Big Lake, MN (US); Joel Phillips, St. Paul, MN (US); Joel R. Munsinger, Duluth, GA (US); David Sogard, Edina, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 394 days.

(21) Appl. No.: 10/010,397

(22) Filed: Nov. 7, 2001

(65) Prior Publication Data

US 2002/0052641 A1 May 2, 2002

Related U.S. Application Data

(62) Division of application No. 09/480,438, filed on Jan. 10, 2000, now Pat. No. 6,322,586.

(51) Int. Cl.[7] .................................................. A61F 2/06
(52) U.S. Cl. ...................................... 623/1.11; 606/108
(58) Field of Search ............................... 623/1.11, 1.12, 623/1.23; 606/108, 192, 198, 195

(56) References Cited

U.S. PATENT DOCUMENTS

| | | | |
|---|---|---|---|
| 4,531,512 A | 7/1985 | Wolvek et al. | |
| 4,531,943 A | 7/1985 | Van Tassel et al. | |
| 4,540,404 A | 9/1985 | Wolvek | |
| 4,649,922 A | 3/1987 | Wiktor | |
| 4,739,769 A | 4/1988 | Matthews et al. | |
| 4,817,613 A | 4/1989 | Jaraczewski et al. | |
| 4,863,442 A | 9/1989 | DeMello et al. | |
| 4,886,506 A | 12/1989 | Lovgren et al. | |
| 4,892,519 A | 1/1990 | Songer et al. | |
| 4,893,623 A | 1/1990 | Rosenbluth | |
| 4,921,483 A | 5/1990 | Wijay et al. | |
| 4,950,227 A | * 8/1990 | Savin et al. ............... | 623/1.11 |
| 4,960,410 A | 10/1990 | Pinchuk | |
| 4,994,018 A | 2/1991 | Saper | |
| 5,017,259 A | 5/1991 | Kohsai | |
| 5,026,377 A | 6/1991 | Burton et al. | |
| 5,041,093 A | * 8/1991 | Chu ........................... | 606/198 |
| 5,078,702 A | 1/1992 | Pomeranz | |
| 5,089,005 A | 2/1992 | Harada | |
| 5,108,416 A | 4/1992 | Ryan et al. | |
| 5,201,757 A | 4/1993 | Heyn et al. | |

(List continued on next page.)

FOREIGN PATENT DOCUMENTS

| | | |
|---|---|---|
| EP | 0 184 314 A1 | 6/1986 |
| EP | 0 408 245 A1 | 1/1991 |
| EP | 0 442 657 A2 | 8/1991 |
| EP | 0 597 465 B1 | 5/1994 |
| EP | 0 627 201 A1 | 12/1994 |
| WO | WO 87/04935 | 8/1987 |
| WO | WO 93/19703 | 10/1993 |

*Primary Examiner*—Kevin T. Truong
(74) *Attorney, Agent, or Firm*—Crompton, Seager & Tufte, LLC (57) ABSTRACT

Methods for making a loaded catheter assembly for delivering a self-expanding stent where the self-expanding stent is carried in a compressed state and the compressed stent has an inside diameter smaller than the outside diameter of the catheter distal tip. The methods can utilize catheter subassemblies lacking already attached tips or having partially formed distal tips. A stent can be proximally and co-axially slid over the distal end of the catheter shaft and constrained by a retractable sheath disposed co-axially about the compressed stent. The catheter distal tip can be added or more fully formed after the loading of the stent. Some catheters include a preformed distal conical tip held in position by a heat-shrink film. Other catheters have an elastomeric distal tip waist for slipping over and engaging an outward projection on the catheter shaft distal region. Some catheters are adapted to engage catheter shaft distal threaded regions.

15 Claims, 10 Drawing Sheets

U.S. PATENT DOCUMENTS

| | | |
|---|---|---|
| 5,201,901 A | 4/1993 | Harada et al. |
| 5,221,270 A | 6/1993 | Parker |
| 5,234,416 A | 8/1993 | Macaulay et al. |
| 5,240,537 A | 8/1993 | Bodicky |
| 5,290,295 A | 3/1994 | Querals et al. |
| 5,318,032 A | 6/1994 | Lonsbury et al. |
| 5,342,386 A | 8/1994 | Trotta |
| 5,370,615 A | 12/1994 | Johnson |
| 5,372,600 A | 12/1994 | Beyar et al. |
| 5,397,345 A | 3/1995 | Lazarus |
| 5,405,380 A | 4/1995 | Gianotti et al. |
| 5,415,664 A | 5/1995 | Pinchuk |
| 5,425,712 A | 6/1995 | Goodin |
| 5,453,090 A | 9/1995 | Martinez et al. |
| 5,480,423 A | 1/1996 | Ravenscroft et al. |
| 5,484,444 A | 1/1996 | Braunschweiler et al. |
| 5,496,294 A | 3/1996 | Hergenrother et al. |
| 5,643,209 A | 7/1997 | Fugoso et al. |
| 5,690,644 A | 11/1997 | Yurek et al. |
| 5,695,499 A | 12/1997 | Helgerson et al. |
| 5,728,063 A | 3/1998 | Preissman et al. |
| 5,769,819 A | 6/1998 | Schwab et al. |
| 5,769,821 A | 6/1998 | Abrahamson et al. |
| 5,827,225 A | 10/1998 | Ma Schwab |
| 5,851,464 A | 12/1998 | Davila et al. |
| 5,919,204 A | 7/1999 | Lukie et al. |
| 6,068,635 A | 5/2000 | Gianotti |
| 6,322,586 B1 | 11/2001 | Monroe et al. |

\* cited by examiner

CATHETER TIP DESIGNS AND METHOD OF MANUFACTURE

This application is a divisional of U.S. application Ser. No. 09/480,438, filed on Jan. 10, 2000 now U.S. Pat. No. 6,322,586.

FIELD OF THE INVENTION

The present invention is related generally to medical devices. More specifically, the present invention is related to catheters. The present invention includes apparatus and methods for affixing catheter tips to stent delivery catheters after a self-expanding stent has been loaded onto the catheter.

BACKGROUND OF THE INVENTION

Heart attacks are a leading cause of death in the industrialized world, particularly in the United States. Many heart attacks are caused in part by a narrowed, stenosed coronary blood vessel. A medical procedure commonly used to deal with coronary vessel stenoses is angioplasty. Angioplasty, in particular Percutaneous Transluminal Coronary Angioplasty (PTCA), includes inserting a balloon catheter into the femoral artery near the groin, and advancing the catheter over the aortic arch and into a coronary artery. The balloon can be advanced through the coronary artery to the stenosis and inflated to widen or dilate the narrowed region. The balloon catheter can then be withdrawn. In some cases, the widened coronary vessel rebounds or re-closes, narrowing the vessel over a period of time.

Stents have come into increasing use to prevent the widened vessel regions from narrowing after angioplasty. A stent, typically having a tubular shape, can be put in place in the widened vessel region to hold the vessel walls apart and the lumen open in the event the vessel attempts to narrow again. One class of stents requires that the stent be forcibly outwardly expanded to put the stent into position against the vessel walls. Another class of stents, self-expanding stents, can be delivered to a site in a compressed or constrained configuration and released in the vessel region to be supported. The self-expanding stent then expands in place to a configuration having a wide lumen, typically pressing firmly against the vessel walls where released. The stent is commonly placed at a recently dilated, stenosed vessel region.

Self-expanding stents can be delivered to a target site mounted over an inner tube or shaft and constrained within the distal end of an enclosing retractable tube or sleeve. The self-expanding stent can be freed from the restraint of the outer sheath by either distally pushing the inner shaft against the stent or proximally pulling the retractable outer sheath from over the stent. Once free of the outer restraint, the self-expanding stent can expand to force itself against the vessel inner walls. Self-expanding stents are often elastically biased to assume an original larger shape after being temporarily compressed into a smaller size to more easily be transported through blood vessels to the target site.

Preferably, the stent is only temporarily compressed within a retractable sheath and compressed for a limited time. The exact size of the stent to be delivered may not be known until the patient is in the operating or treatment room of a hospital. In general, a catheter should have a maximum radial extent or profile no larger than necessary, in part to enable the catheter to reach further into narrower vessel regions. A self-expanding stent is most easily loaded in a proximal direction onto a catheter by compressing the stent and sliding the stent co-axially over the inner shaft distal end and within the retractable outer sheath. The stent must thus typically be slid over the catheter distal tip. The distal tip is optimally tapered, having a proximal width about the same as the width of the outer sheath, to provide a smooth transition from the distal tip to the outer sheath. This can present a situation where the compressed stent has an inner diameter too small to be advanced over the larger outer diameter distal tip of the catheter.

What would be desirable is a delivery catheter and method which would ease loading of a self-expanding stent by not having the tip on the delivery system at the time of loading. This would allow the self-expanding stent to be slid under the sheath with subsequent tip attachment.

SUMMARY OF THE INVENTION

The present invention includes a loaded, self-expanding stent delivery catheter assembly having an inner shaft or tube, a retractable sheath disposed over the inner shaft, and a compressed, self-expanding stent disposed co-axially between the inner shaft and retractable sheath. The inner shaft is a solid shaft in some embodiments, and a hollow shaft or tube having at least one lumen therethrough in other embodiments. The inner shaft terminates distally in a tip, preferably tapered, which can have a profile sufficiently large, such that the compressed stent cannot be passed proximally over the distal tip when mounted on the catheter distal end. The catheter assembly includes a distal tip adapted to be easily secured to the inner shaft after the stent has been proximally loaded over the catheter distal end. The present invention also allows attachment of catheter tips to tubes even after the tubes have been coated with material which are incompatible with later adhesive use.

One catheter includes a shrinkable film secured to the catheter inner shaft distal end and having a sufficiently small profile when collapsed or pressed against the inner shaft to allow the stent to be passed over the film, and onto the catheter distal region. After the stent is loaded, the tip is added by co-axially sliding a preformed conical tip over the inner shaft and under the shrinkable film and securing the tip to the inner shaft by shrinking the film over the tip and inner shaft. One embodiment utilizes heat-shrinkable film. One embodiment secures the film proximally to the inner shaft with outwardly projecting barbs or ridges. Another embodiment bonds the shrinkable film to the inner shaft.

In one set of embodiments, the distal tip has a proximal region allowing outward projections from the inner shaft to extend and cut into the region wall and secure the tip to the inner shaft. In some embodiments, the proximal region wall is sufficiently elastic to allow the proximal region to expand and contract when passed over the projections. In some embodiments, the proximal region is swollen with solvent to pass over the projections and the solvent later flashed off. In some embodiments, the proximal region wall has internal recesses or channels partially through the wall to receive outward projections from the inner shaft. In other embodiments the wall has holes or slots entirely through the wall. The proximal region holes or slots can be used to secure the tip to the inner shaft by allowing outward projections to fit through the openings, inhibiting the distal tip from moving relative to the inner shaft.

One catheter distal region according the present invention has a first configuration as a distal sleeve or tube, allowing a compressed stent to be passed over the tube. The tube can then be formed into a catheter distal tip by heating and reforming the tube material into a tip such as a conical tip having a lumen therethrough. One distal tip includes a proximal threaded region adapted to be threadably secured to a corresponding distal threaded region on the inner shaft. Another distal tip includes a proximal coil adapted to secure the tip to a corresponding distal threaded region on the inner shaft.

One group of distal tips according to the present invention is already attached to the inner shaft, but in a compressed or low profile state, and expands radially after a compressed stent has been passed proximally over the tip. One distal tip is formed of a reversibly compressible material which can be constricted by a compression tube while the stent is passed over the tube and allowed to expand to a larger profile by removing the compression tube. Another distal tip is formed of a swellable material which is chemically swollen to a larger outside diameter after a stent is allowed to pass over the tip and onto the distal region of the inner shaft. One suitable tip material is water-swellable and the tip is hydrated after the stent is in place.

DETAILED DESCRIPTION OF THE INVENTION

Figure 1:
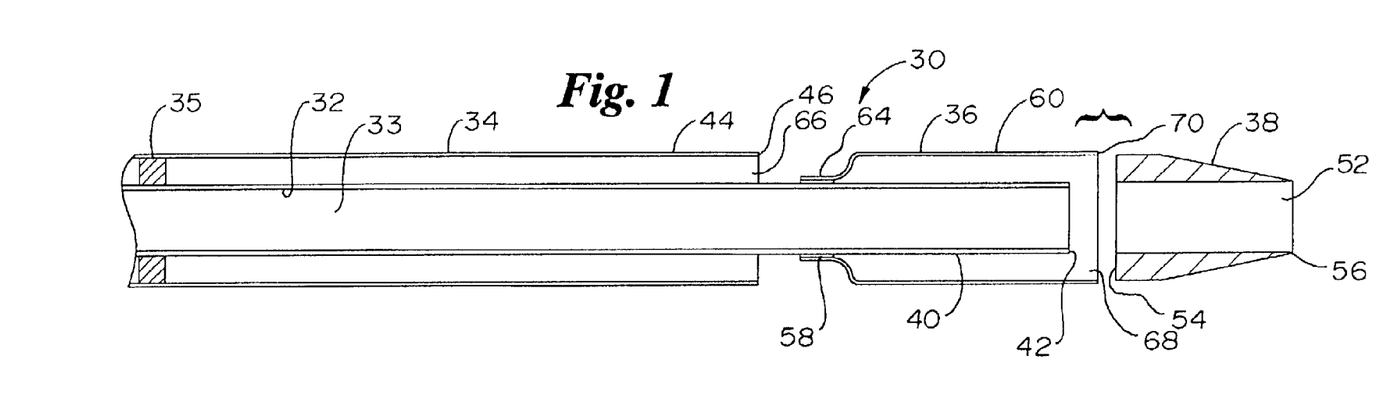
FIG. 1 is a fragmentary, side, cross-sectional view of a stent delivery catheter in assembly, having an inner shaft, a retractable sheath thereover, a distal sleeve of heat-shrinkable material bonded thereto, and a preformed distal cone.

FIG. 1 illustrates a stent delivery catheter assembly 30 in the process of manufacture. Catheter assembly 30 includes an inner tube 32 having a lumen 33 therethrough, a distal region 40 and a distal end 42. Inner tube 32 is preferably formed of a polymeric material suitable for delivering a stent through tortuous vessel passages and suitable for receiving a guidewire therethrough. One suitable material includes braided polyimide tubing. A retractable sheath 34 having a distal region 44 and a distal end 46 is slidably disposed over inner tube 32, having an annular space 66 sufficient in size to receive a compressed stent between inner tube 32 and retractable sheath 34. Retractable sheath 34 can be formed of a polymeric material preferably sufficiently lubricious to ease in advancing catheter assembly 30 through increasingly smaller blood vessels. Sheath 34 can be formed of materials such as high density polyethylene or nylon. A stop 35 is affixed to the inner tube 32 proximal of its distal end, about the length of a stent 50 (shown in FIG. 2). The stop functions to hold the stent axially during deployment relative to the outer tube 34.

A distally positioned film or sleeve 36 is disposed over inner tube distal region 40 and is affixed to inner tube 32 as indicated at 58. Sleeve 36 is preferably formed of a shrinkable film material, for example a heat-shrinkable material such as polyolefin copolymer, nylon, or polytetrafluoroethylene. Sleeve 36 can be secured to inner tube 32 using heat bonding, adhesives, or solvent welding, using methods well known to those skilled in the art. Sleeve 36 can include a waist portion 64 and a free portion 60. Sleeve 36 is illustrated having an open distal end 70 and an annular space 68 for receiving a distal cone, described later. While film 36 is illustrated in a tubular sleeve configuration, other film geometries are also within the scope of the invention.

Distal tip 38 is illustrated having a lumen 52, a proximal end 54, and a distal end 56. Tip 38 is preferably tapered to aid in tracking catheter 30 through vessel passages and turns.

Tip 38 is conically tapered in one embodiment and has a curved or arcuate taper in another embodiment.

Figure 2:
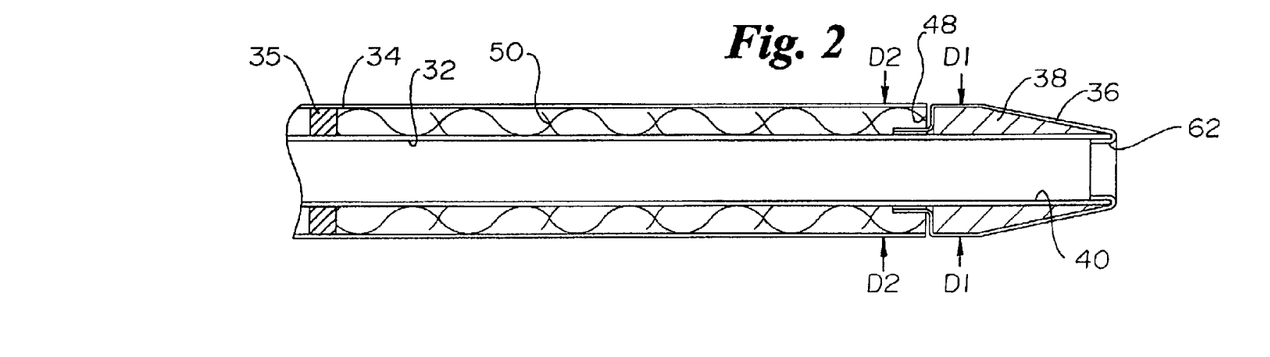
FIG. 2 is a fragmentary, side, cross-sectional view of the catheter of FIG. 1, having an expandable stent loaded between the inner shaft and retractable sheath and the distal cone affixed distally to the inner shaft with the heat-shrink distal sleeve.

FIG. 2 illustrates catheter assembly 30 in a later stage of assembly, having a self-expanding stent 50 inserted into annular space 66 between retractable sheath 34 and inner tube 32. Stent 50 can be placed over inner tube 32 by sliding stent 50 proximally over inner tube distal end 42, and over distal sleeve 36. Sleeve 36 can be drawn distally or otherwise decreased in outer diameter, such as by compressing, to allow stent 50 to pass proximally over the sleeve. Stent 50 is preferably compressed using a suitable tool or jig, to decrease the outer diameter of the stent. With the stent preferably compressed, the stent can be axially and proximally slid over inner tube 32 and within sleeve distal region 44, to reside in annular space 66. With the stent constrained by retractable sleeve 34, any restraining tool or jig can be removed from the catheter.

With stent 50 in position, tip 38 can be affixed to inner tube 32. Tip lumen 52 can be slid axially and proximally within annular space 68 over inner tube 32 and within distal sleeve 36. Tip 38 has a maximum radial extent indicated as "D1" in FIG. 2. D1 is preferably dimensioned such that tip 38 can be slid within annular space 68. Retractable sheath 34 has a distal radial extent indicated as "D2" in FIG. 2. In one embodiment, D1 and D2 are approximately equal, such that when tip 38 abuts retractable sleeve 34, the outer diameter is approximately constant over the transition. In another embodiment, tip outer diameter D1 is larger than sleeve distal diameter D2, such that tip 38 can sufficiently dilate narrow vessels to pass over tip and over retractable sleeve distal end 46.

Figure 4:
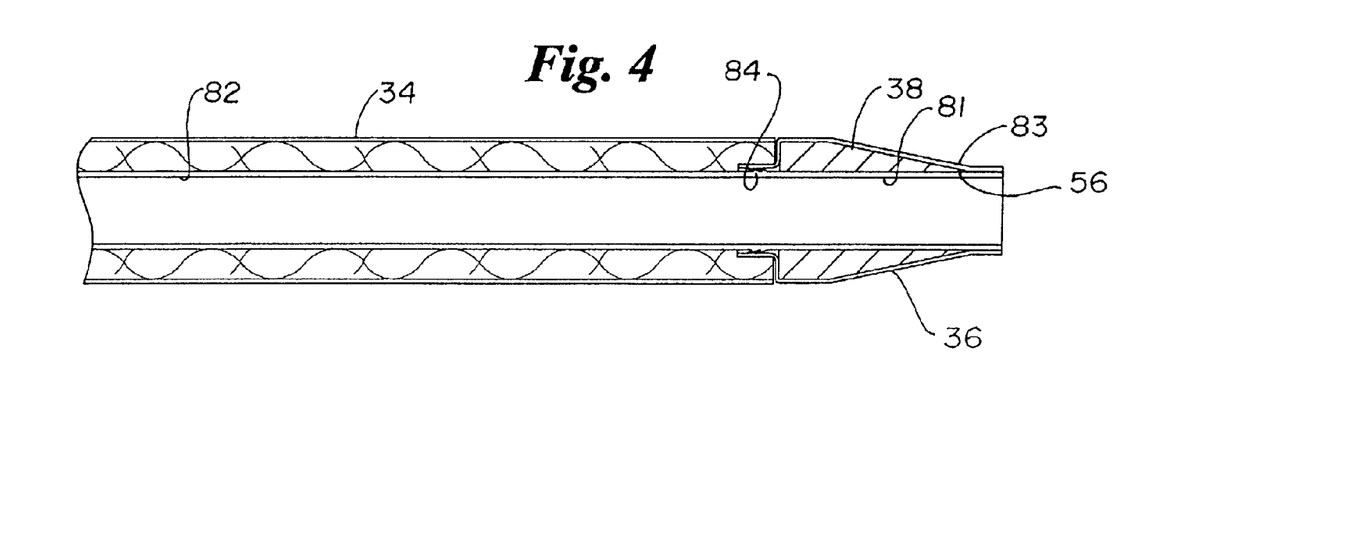
FIG. 4 is a fragmentary, side, cross-sectional view of the catheter of FIG. 3, having the distal cone fixed in position over the inner shaft, and a heat-shrinkable sleeve disposed over the barbs and cone.

With tip 38 slid within shrinkable film or sleeve 36, the film material can be tucked over the tip and within inner tube 32, as indicated in a tucked or draped portion 62. Alternatively, the film material may extend distally and have a distal portion inner surface in contact with the outer surface of the inner tube, both of which extend distally beyond the distal end of the tip. This alternative is depicted in the embodiment of FIG. 4. The film material can be shrunk over tip 38, thereby securing tip 38 in place over inner tube distal region 40. As illustrated in the example of FIG. 2, stent 50 is dimensioned such that the stent could not have been slid over inner tube 32 and within sheath 34 if tip 38 had been in place. The present invention allows the stent to be positioned proximally of the ultimate location of the distal tip by allowing the stent to be slid proximally over the shrinkable film material rather than over the tip. The present invention allows the tip to be affixed to the inner tube after the stent has been mounted over the tube.

Figure 3:
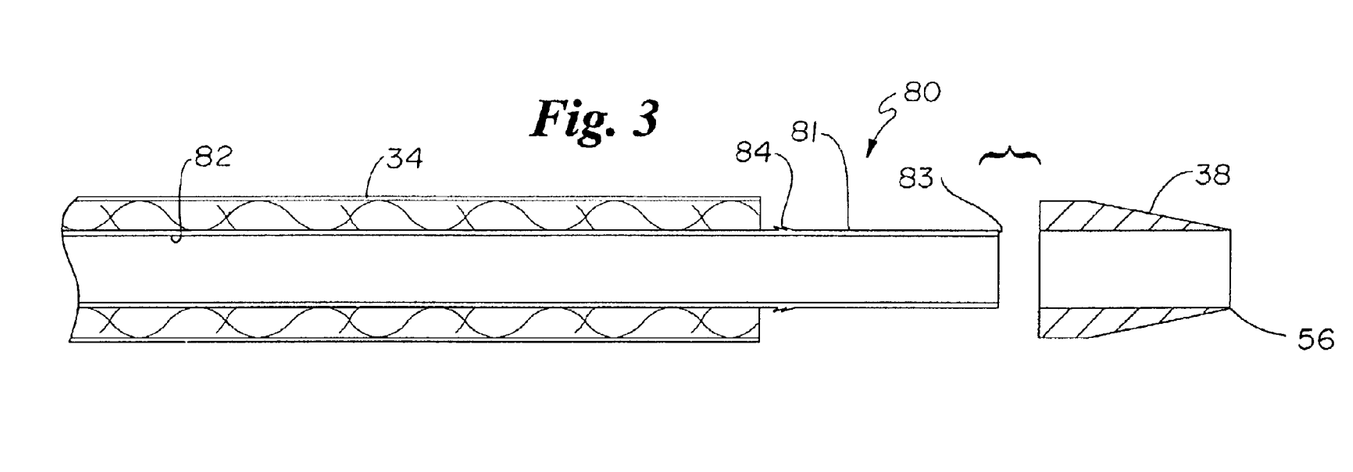
FIG. 3 is a fragmentary, side, cross-sectional view of a stent delivery catheter in assembly, having an inner shaft with distal barbs, a constrained stent and retractable sheath thereover, and a preformed distal cone.

Referring now to FIG. 3, another catheter assembly 80 is illustrated. Catheter assembly 80 is similar is some respects to catheter assembly 30 of FIGS. 1 and 2, with catheter assembly 80 having an inner tube 82 having a distal end 83 and having outward projections or barbs 84 disposed in an inner tube distal region 81. Barbs 84 provide one method for securing a shrinkable film to inner tube 82, as an alternative to bonding. FIG. 3 illustrates stent 50 already positioned over inner tube 82 and constrained by retractable sleeve 34. Distal tip 38 is also illustrated, in position for further assembly.

Referring now to FIG. 4, distal tip 38 is illustrated as secured in position by shrinkable film 36 draped over barbs 84. To manufacture the embodiment illustrated in FIG. 4, distal tip 38 can be slid axially over inner tube 82. Shrinkable film or sleeve 36 can be slid over or wrapped around both tip 38 and inner tube barbs 84. As shown in FIG. 4, the distal portion of the film 36 and a distal portion of the inner tube may extend beyond distal end 56 of tip 38 to bond to one another. Shrinking the film can bond the film to both tip and inner tube, with barbs 84 engaging film 36. In one embodiment, film 36 is draped over distal tip distal end 56 and shrunk to further secure tip 38 to inner tube 82. In one embodiment, inner tube distal end 83 is softened and splayed outward about distal tip distal end 56 to further secure tip 38 to inner tube 82. In one method inner tube distal end 83 is heated and pressed into a concave die to form a slightly mushroomed tip. Inner tube 82 can also be further bent back around tip distal end 56 as illustrated in FIG. 4. Barbs 84 can thus provide a device for securing film 36 to inner tube 82.

Figure 5:
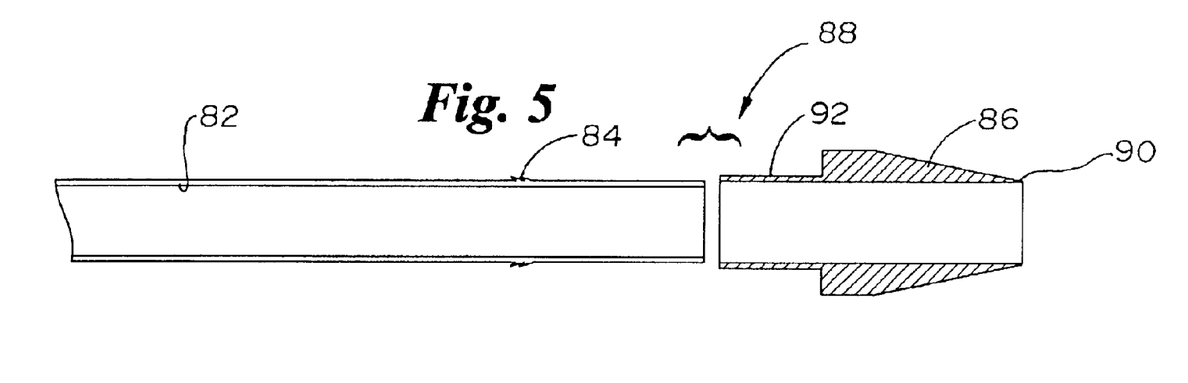
FIG. 5 is a fragmentary, side, cross-sectional view of a catheter in assembly including an inner shaft having distal barbs, and a distal tip.
Figure 6:
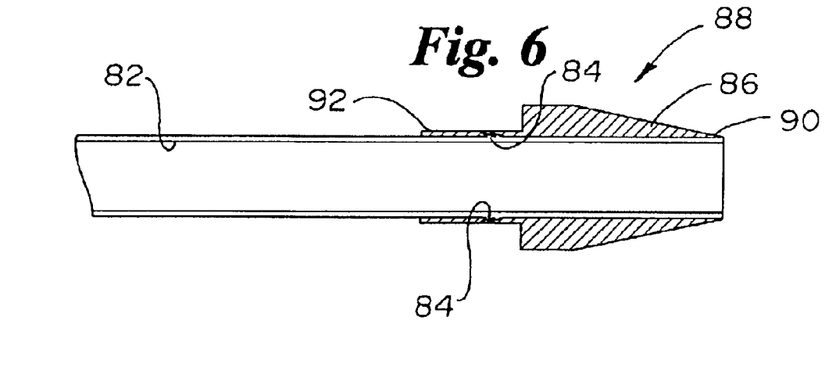
FIG. 6 is a fragmentary, side, cross-sectional view of the catheter of FIG. 5, having the distal tip slipped over and secured to the distal barbs.

Referring now to FIGS. 5 and 6, a catheter assembly 88 is illustrated in the process of assembly, having inner tube 82 with barbs 84 and a distal tip 86. The self-expanding stent and retractable sleeve have been omitted for simplicity. Distal tip 86 has a proximal sleeve or waist portion 92, a distal tip portion 90, and is preferably formed of a polymeric material adapted to slip over barbs 84. In one embodiment, the polymeric material elastically expands to accommodate barbs 84, then contracts again proximal of barbs 84. FIG. 6 illustrates proximal waist 92 in place over barbs 84. In one embodiment, the polymeric material is swollen with solvent, waist 92 forced over barbs 84, and the solvent flashed off, shrinking the waist over the barbs. Using solvent to swell film sleeves followed by flashing off solvent can be used in other embodiments as well. Barbs 84 can bite into proximal sleeve portion 92 to secure tip 86 to inner tube 82 or alternatively, sleeve portion 92 can form around barbs 84 to provide a mechanical lock.

The embodiment of FIGS. 5 and 6 allow a stent and retractable sleeve to be axially slid over the distal end of an inner tube prior to securing the distal tip to the inner tube. In one embodiment, a discrete number of barbs are distributed around the inner tube outer wall. In one embodiment two barbs are present while other embodiments have three and four barbs. In one embodiment, the barbs are formed as sharp, proximally inclined annular ridges surrounding the inner tube rather than as a discrete barbs. The embodiment of FIGS. 5 and 6 allow a distal tip to be secured by sliding the tip over the inner tube distal end after the expandable stent has been slid into place.

Figure 7:
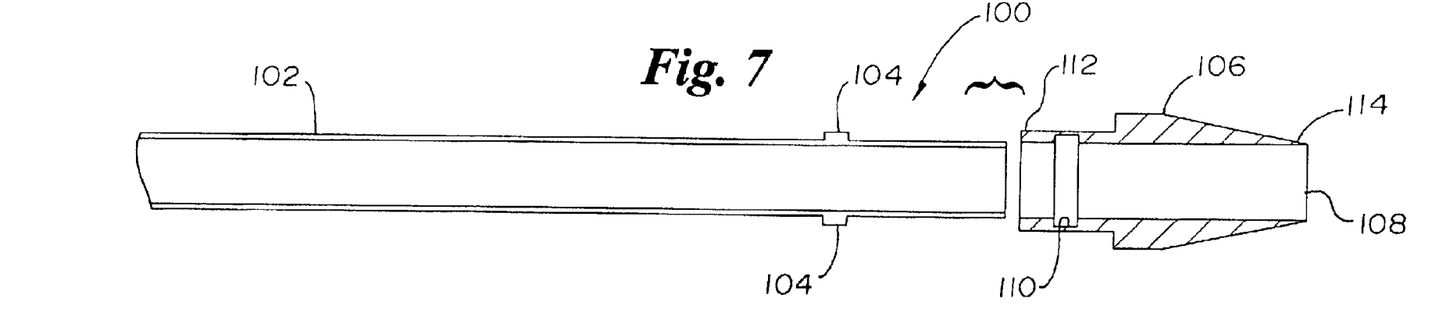
FIG. 7 is a fragmentary, side, cross-sectional view of a catheter in assembly having an inner shaft with a distal annular ridge.
Figure 8:
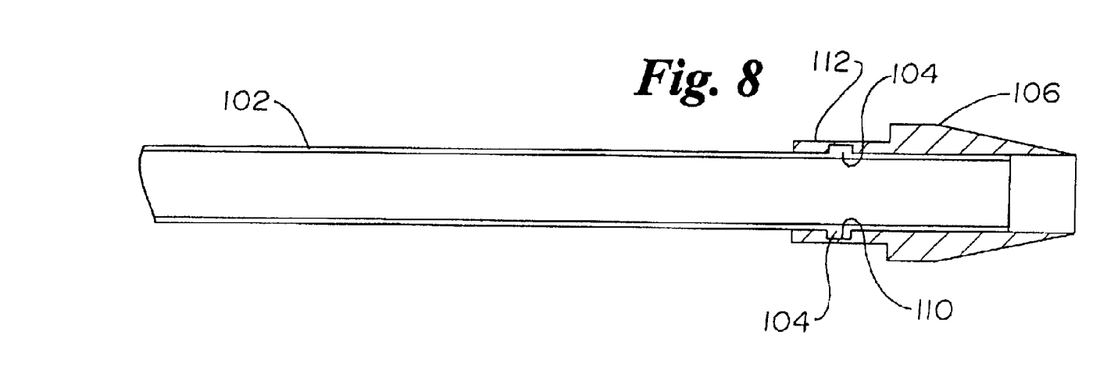
FIG. 8 is a fragmentary, side, cross-sectional view of the catheter of FIG. 7, having a matching distal tip with an annular channel fit over the inner shaft annular ridge.

Referring now to FIGS. 7 and 8, another catheter assembly 100 is illustrated in the process of assembly, having an inner tube 102 and a distal tip 106. Inner tube 102 includes outward protrusions 104. Outwardly directed protrusions 104 can be formed as a series of discrete outward protrusions, as a single continuous annular ring, or as a series of discrete annular ring segments. Distal tip 106 includes a distal end 114, a proximal sleeve or waist portion 112, a lumen 108, and an inner detent or recess 110. Inner recess 110 can include a series of discrete recesses, a single annular channel, or a series of annular channel segments. Inner recess 110 is preferably matched to receive outward protrusions 104 on inner tube 102. In FIG. 8, inner tube 102 has been inserted into distal tip 106, causing outward protrusions 104 to fit into inner recess 110. The self-expanding stent and retractable sleeve have been omitted for clarity. Distal tip waist 112 is preferably formed of a sufficiently elastic material to expand and slide over outward protrusions 104 until the protrusions are fit within the inner recess of the distal tip. The embodiment of FIGS. 7 and 8 thus allows a stent to be slid over the inner tube and constrained by a retractable sheath, followed by attachment of the distal tip to the inner tube.

Figures 9, 10:
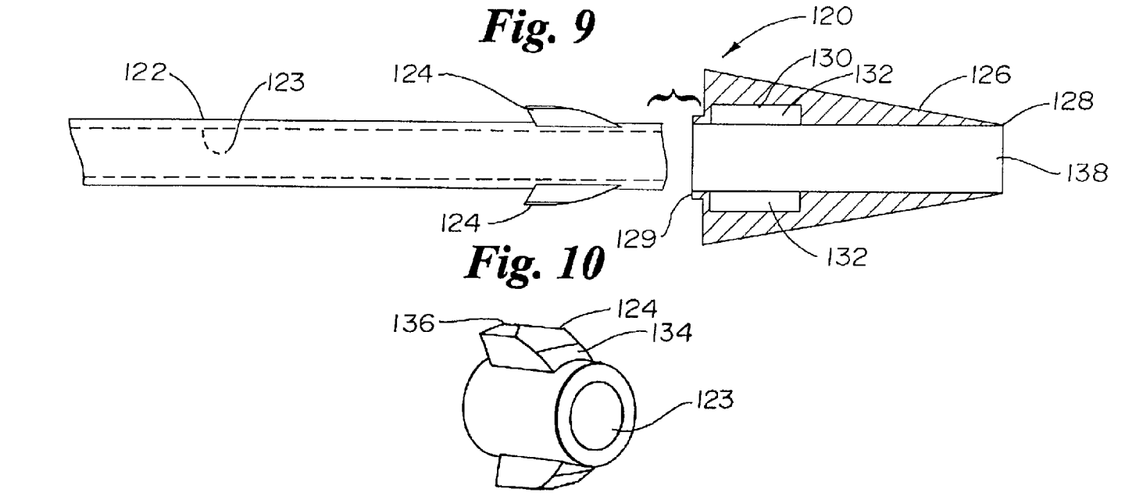
FIG. 9 is a fragmentary, side, cross-sectional view of a catheter in assembly having an inner shaft with distal fins and a distal tip with receiving slots for securing the tip to the inner shaft fins.
FIG. 10 is a fragmentary, perspective view of the inner shaft and distal fins of FIG. 9.
Figure 11:
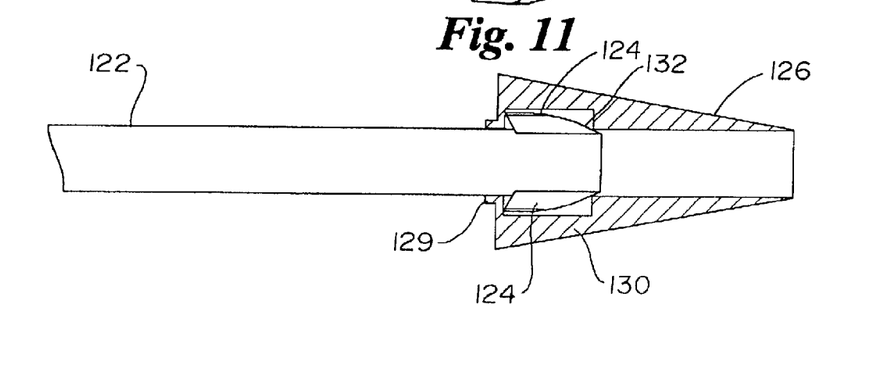
FIG. 11 is a fragmentary, side, cross-sectional view of the catheter of FIG. 9, after the distal tip slots have been fit over the inner shaft fins.

Referring now to FIGS. 9, 10, and 11, another catheter assembly 120 in the process of assembly is illustrated, having an inner tube 122 and a distal tip 126. Inner tube 122 has a lumen 123 therethrough and has outwardly directed protrusions or fins 124 mounted on the external inner tube walls. Distal tip 126 includes a distal end 128, a proximal end 129, a proximal waist 130, a lumen 138 therethrough, and openings or slots 132 through the wall of distal tip waist region 130. FIG. 10 further illustrates one embodiment of fins 124, illustrating two fins 124 having a distal ramp region 134 and a more proximal land region 136. More or less than two fins can be utilized. Fin ramps 134 can serve to force a sufficiently elastic tip sleeve or waist region to expand over the fins. FIG. 11 illustrates distal tip 126 forced proximally over fins 124 until the fins protrude through slots 132, securing distal tip 126 to inner tube 122. During assembly, a self-expanding stent can be slid proximally of fins 124 and constrained by a surrounding retractable sheath. After placement of the stent, the distal tip can be slid proximally over the fins, securing the tip to the inner tube.

Figure 12:
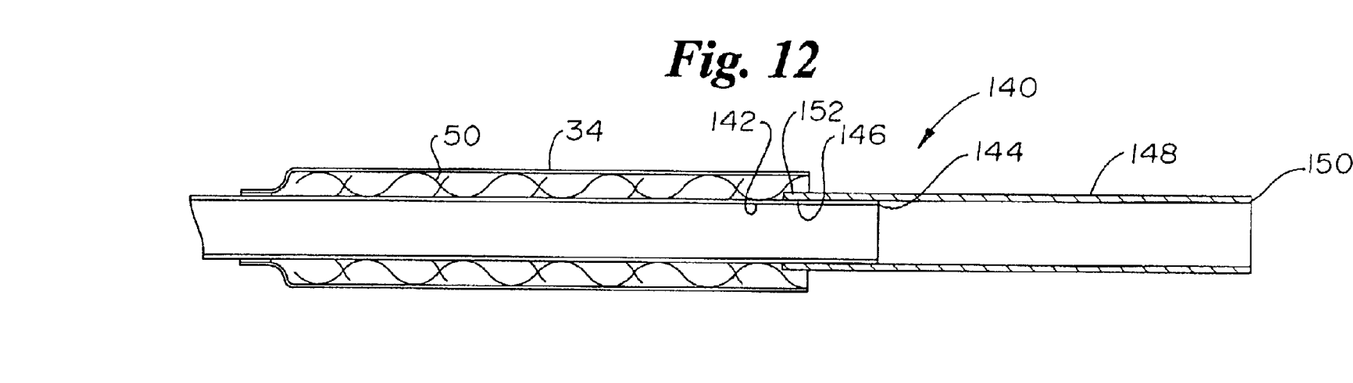
FIG. 12 is a fragmentary, side, cross-sectional view of a catheter in assembly having an inner shaft, a constrained stent and retractable sheath thereover, and a proximally bonded distal polymer sleeve.

Referring now to FIG. 12, another catheter assembly 140 is illustrated in the process of being assembled. Catheter assembly 140 is illustrated having stent 50 and retractable sheath 34 already in place over an inner tube 142 having a distal end 144. A distal sleeve or tube 148 having a distal end 150 and a proximal end 152 is bonded at a bonding region 146 to inner tube 142. In one embodiment, distal tube 148 is flexible while in another embodiment distal tube 148 is rigid. Distal tube 148 is preferably formed of a thermosetable polymeric material such as polyurethane or polyamide. Stent 50 can be proximally inserted over distal tube 148 and inner tube 142 while the distal tube is in the configuration illustrated in FIG. 13, in which distal tube 148 can have an outer diameter approximately equal to that of inner tube 142.

Figure 13:
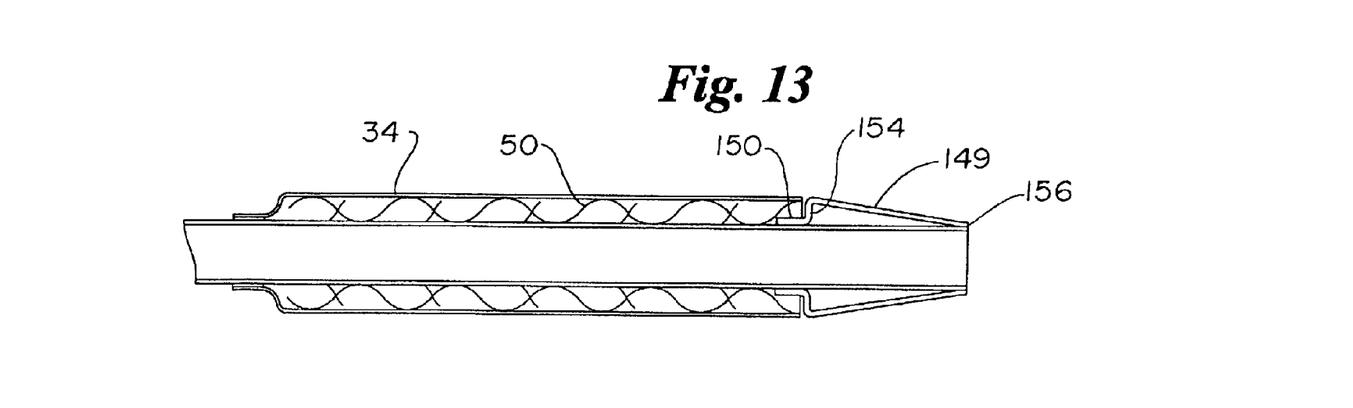
FIG. 13 is a fragmentary, side, cross-sectional view of the catheter of FIG. 12, having the distal sleeve formed into a distal tip.

After stent 50 has been positioned over inner tube 142 and constrained by retractable sleeve 34, distal tube 148 can be formed into a distal tip 149 as indicated in FIG. 13. In the embodiment illustrated in FIG. 13, the distal sleeve has been pushed back to form a proximal wall portion 154 substantially transverse to the catheter longitudinal axis. In this embodiment, the sleeve has been tapered distally, ending at a distal tip portion 156 where the sleeve can be bonded to the inner tube. The distal sleeve can be heated to reform the sleeve, and the sleeve allowed to cool and set in the new, conically tapered shape. In some methods, the sleeve is formed into the desired shape with a heated mold or die. In one method, the distal end of distal sleeve 148 is tucked back inside itself and the proximal end of distal sleeve 148 bunched back and expanded in diameter such that the sleeve assumes a conically tapered shape with the sleeve forming both an internal and an external wall. In some embodiments, the distal tip is formed from a substantially remelted polymeric sleeve such that the distal tip has a substantially solid configuration. In embodiments allowing for use of a guide wire, the tip can be shaped to allow for passage of a guide wire lumen therethrough. The distal sleeve thus allows for slipping a stent proximally over the sleeve while the sleeve is in the small diameter configuration. The distal sleeve then allows for reformation of the sleeve into a distal tip for use in delivering the stent.

Figure 14:
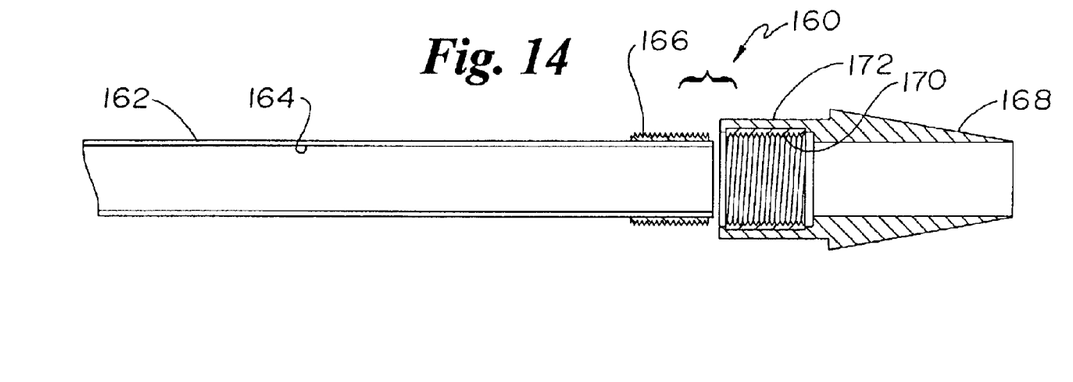
FIG. 14 is a fragmentary, side, cross-sectional view of a catheter assembly having an externally threaded inner shaft and an internally threaded catheter tip.
Figure 15:
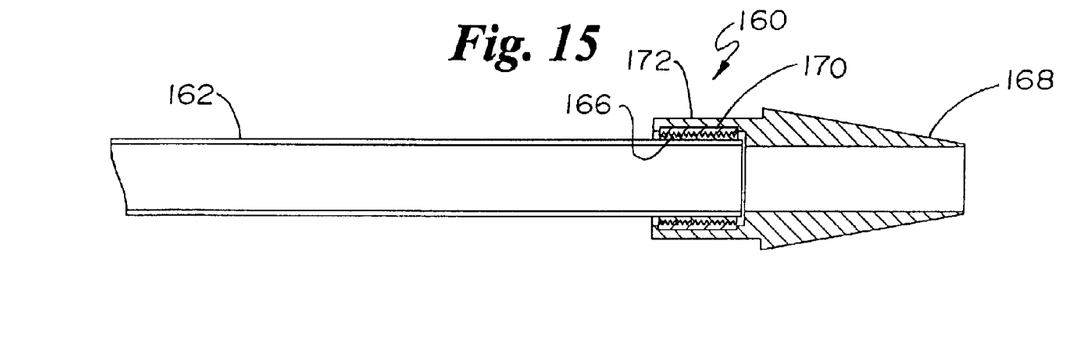
FIG. 15 is a fragmentary, side, cross-sectional view of the catheter assembly of FIG. 14, having the tip threaded onto the inner shaft.

Referring now to FIGS. 14 and 15, FIG. 14 illustrates a catheter assembly 160, having an inner tube 162 and a not yet attached distal tip 168. Inner tube 162 has a lumen 164 therethrough and a distal exterior threaded region 166. Distal tip 168 has a proximal waist region 172 including a proximal interior threaded region 170. In the embodiment illustrated, the tube distally threaded region is externally threaded, for later attachment of the internally threaded tip.

FIG. 15 illustrates inner tube 162 threadably secured to distal tube 168. In another embodiment, not requiring illustration, the inner tube is internally threaded for mating to the externally threaded proximal waist of a distal tip adapted to be received within the inner tube distal end. The threaded regions of the inner tube and the distal tip allow the distal tip to be secured to the inner tube after a stent has been loaded over the inner tube distal end.

In one method, threads are cut on the outside of a hypotube section which can be bonded to the outside of a tube requiring outer threads. Threads can be cut on the inside of another hypotube section which can be bonded to the inside of the tube to receive inner threads. The hypotube sections can be insert molded into the catheter tubes and distal tip. Threads could also be molded or cut into the inside diameter of a polymer tip.

Figure 16:
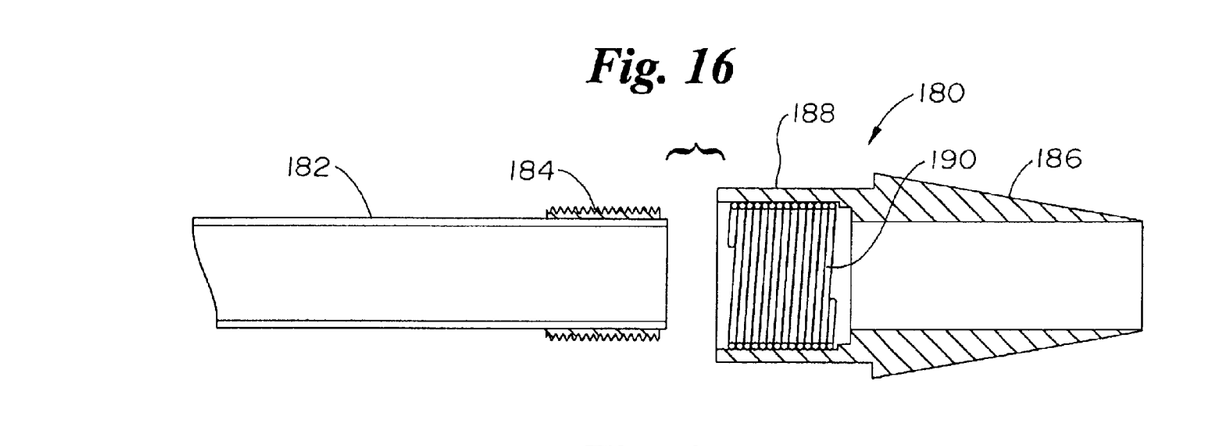
FIG. 16 is a fragmentary, side, cross-sectional view of a catheter assembly having an externally threaded inner shaft and a catheter tip, comprised of a coil, adapted to secure the tip to the inner shaft threads.

Referring now to FIG. 16, another catheter assembly 180 prior to final assembly is illustrated. An inner tube 182 has a distally threaded or scored region 184. A distal tip 186 includes a proximal waist region 188 and an internally mounted coil 190. Coil 190 is dimensioned so as to securably engage inner tube threaded region 184 when distal tip 186 is rotatably advanced over inner tube 182. The threaded region on inner tube 182 includes a series of concentric annular grooves in one embodiment and a single helical groove in another embodiment. The distal tip internal coil allows securing the distal tip to the inner tube after a stent has been proximally slipped over the inner tube distal end.

Figure 17:
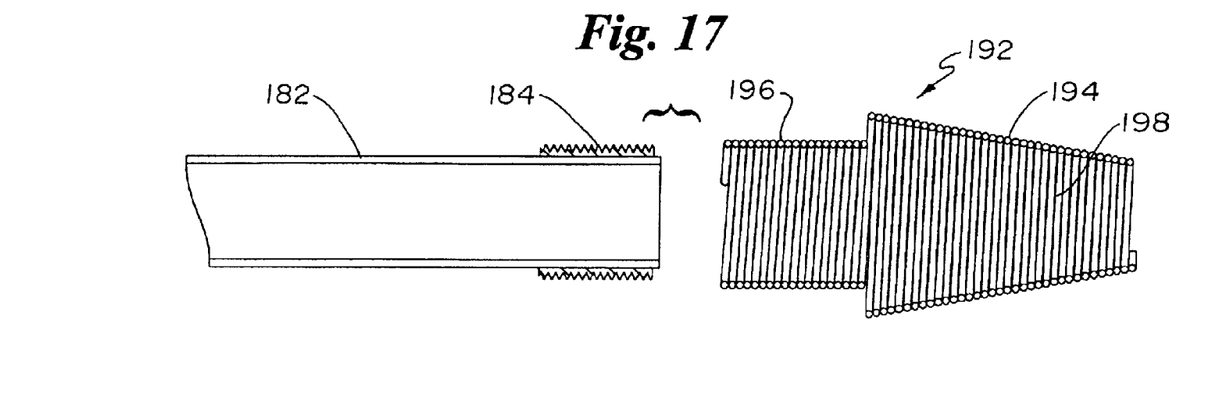
FIG. 17 is a fragmentary, side, cross-sectional view of a coiled catheter tip adapted to be secured to the inner shaft threads of FIG. 15.

Referring now to FIG. 17, inner tube 182 having distally threaded or scored region 184 is again shown, in the process of being secured to a distal tip 192 having a waist region 196 and formed of a coil 194 having a plurality of helically wound strands 198. Tip 192 can be formed entirely of a coil. Coil proximal waist region 196 is adapted to be secured to inner tube threaded region 184 by rotatably advancing the tip of the distal end over the inner tube. In the embodiment illustrated in FIG. 17, the inner tube is externally threaded and the tip is adapted to be mounted externally over the inner tube. In another embodiment, not requiring illustration, the inner tube is internally threaded and the distal tip is dimensioned to be received within the inner tube distal end.

The inner diameter of the coil can be less than the minor diameter of the threads. The coils on the tip can be coiled so that when the coil is torqued to put the tip onto the shaft, the coil grows in diameter and the torque required to put the tip onto the inner tube is reduced. The coil can then cinch down onto the threads when the coil is torqued to remove it from the inner tube. The coils on the tip can be coiled so that the space between the coils is less than the pitch of the threads on the inner tube. This creates friction between the coil and the teeth of the threads, which can also prevent the distal tip from coming off the inner tube. Threads can be cut into a section of hypotube bonded or insert molded into the inner tube. Threads can also be formed of a coiled wire bonded to the inner tube wall.

Figure 18:
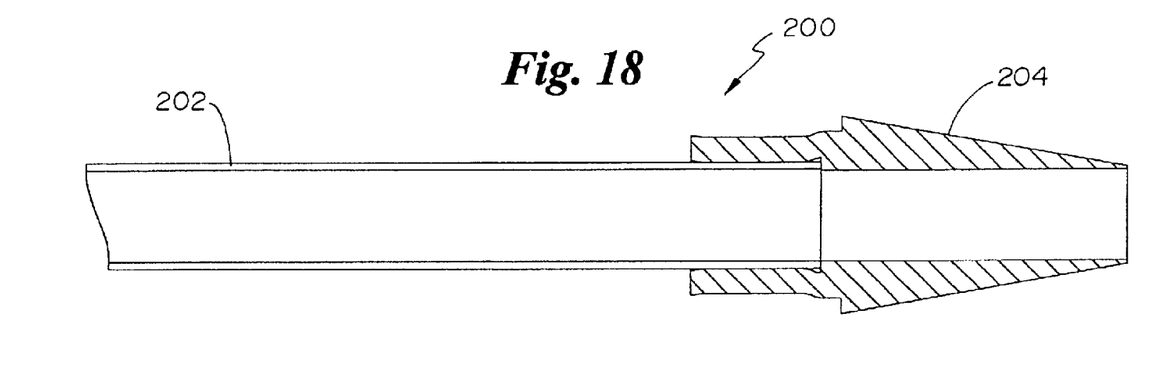
FIG. 18 is a fragmentary, side, cross-sectional view of a catheter distal region having an unconstrained, compressible distal tip.
Figure 19:
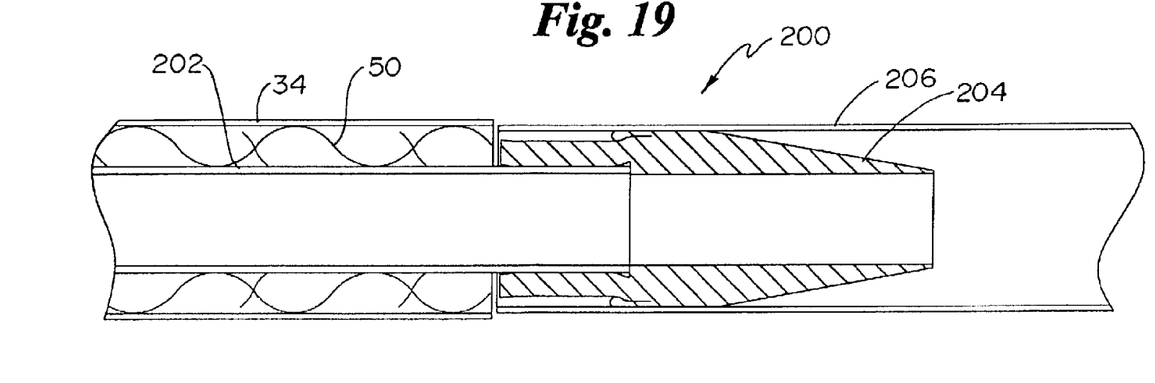
FIG. 19 is a fragmentary, side, cross-sectional view of the catheter of FIG. 18, having the tip compressed with a compression tube and an expandable stent fit between the inner shaft and a retractable sleeve.

Referring now to FIGS. 18 and 19, a catheter assembly 200 having an inner tube 202 and a compressible distal tip 204 is illustrated in an assembly process. Compressible distal tip 204 is shown in an expanded, unconstrained configuration. Distal tip 204 can be made of a compressible polymeric material such as silicone (i.e., polydimethylsiloxane) or polystyrene. FIG. 19 illustrates catheter assembly 200 having a compression tube 206 forced proximally over distal tip 204, thereby compressing the tip within the compression tube, causing the tip to have a reduced outer diameter. With the compression tube in place, stent 50 can be slid proximally over compressed tip 204 and compression tube 206, to be restrained within retractable sheath 34. Once stent 50 is in position, compression tube 206 can be retracted distally, allowing distal tip 204 to expand such that the radial outer extent of the distal tip is at least about as large as that of the retractable sheath distal end.

Figure 20:
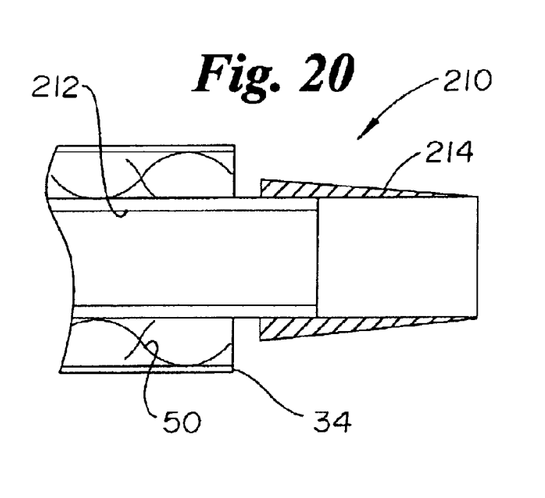
FIG. 20 is a fragmentary, side, cross-sectional view of a catheter in assembly having an inner shaft, an expandable stent and retractable sleeve slid thereover, and an expandable or swellable distal tip.
Figure 21:
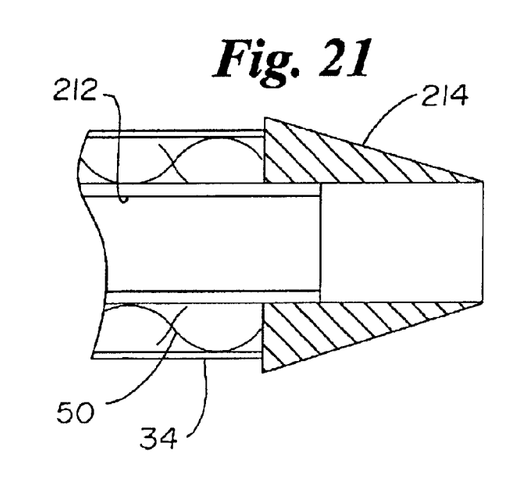
FIG. 21 is a fragmentary, side, cross-sectional view of the catheter of FIG. 20, after the distal tip has been expanded.

Referring now to FIGS. 20 and 21, a catheter assembly 210 having an inner tube 212 and a swellable distal tip 214 is illustrated in the process of assembly. In FIG. 20, stent 50 and retractable sheath 34 have already been placed in position. In the compressed configuration, distal tip 214 has a sufficiently small profile to allow stent 50 to pass proximally over the tip and within the retractable sheath. Once stent 50 is in position, swellable tip 214 can be expanded in profile, or swollen, by adding water or another chemical suitable to swell the distal tip material in size. Examples of material suitable for making a swellable tip include hydrogels and polystyrene. Examples of solvents or compounds suitable for swelling the distal tip include isopropyl alcohol, heptane, water, xylene, and toluene. FIGS. 21 and 22 thus illustrate devices and methods for providing a catheter which can be loaded with an expandable stent while the distal tip is small in profile. The distal tip can later be increased in size by swelling the catheter tip to provide a distal tip having a profile at least as large as that of the retractable sheath distal end.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method for assembling a loaded, self-expanding stent delivery catheter comprising the steps of:

providing a shaft, a retractable sheath, a self-expanding tubular stent, said shaft, stent, and sheath cooperatively sized so as to allow co-axially receiving said stent between said shaft and said sheath, said shaft having a distal region and a distal end with at least one outward projection in said distal region, said sheath having a distal region and a distal end, said stent having a distal end;

providing a tapered tip having a lumen therethrough, a proximal region, and a proximal end;

positioning said sheath co-axially over said shaft such that said sheath distal end is positioned near said shaft distal region;

positioning said compressed stent proximally co-axially over said shaft such that said stent distal end is disposed near said shaft distal region and said stent is radially constrained by said sheath distal region;

disposing said tip co-axially over said shaft such that said tip proximal end is positioned near said shaft distal region; and forcing said tip proximal region co-axially over said shaft outward projections such that said tip is caught on said projections and secured to said shaft.

2. A method as recited in claim 1, wherein said shaft outward projection has sharp outwardly extending edges and said tip proximal region includes an elastic wall and said forcing step includes stretching elastic wall over said sharp edges such that said edges cut at least partially through said elastic wall.

3. A method as recited in claim 1, wherein said tip proximal region lumen includes an internal recess adapted to received said shaft outward projection, said tip proximal region includes an elastic wall, and said forcing step includes stretching said elastic wall over said projection such that said projection extends into said internal recess.

4. A method as recited in claim 3, wherein said tip proximal internal recess is an annular channel and said projection is at least one annular ring and said forcing step includes forcing said elastic wall over said ring until said wall annular channel fits over said at least one annular ring.

5. A method as recited in claim 4, wherein said tip has a proximal region including a wall having at least one hole therethrough adapted to receive said shaft projection and said forcing step includes forcing said tip proximal region proximally over said projection and stretching said wall until said projections extends through said tip proximal region wall.

6. A method as recited in claim 5, where said tip includes a proximal waist and said hole through said wall is disposed in said waist.

7. A method as recited in claim 5, wherein said shaft outward projection includes at least on longitudinally oriented fin, said tip includes a proximal waist, said hole through said wall is disposed in said waist, said hole has a longitudinally oriented slot shaped to receive said fin, and said forcing step includes forcing said fin through said slot.

8. A loaded, self-expanding stent delivery catheter assembly comprising:

a shaft having a distal end, a distal region, and at least one outwardly extending projection in said shaft distal region;

a retractable sheath having a distal region and a distal end disposed axially over said shaft distal region such that said sheath distal end is positioned proximally of said shaft distal end;

a self-expanding tubular stent co-axially disposed over said shaft distal region and disposed co-axially within said sheath distal region, such that said stent is radially constrained by said sheath distal region; and a distal tip co-axially disposed over said shaft distal region substantially distally of said sheath distal region, said tip secured to said shaft, wherein said tip has a proximal region wall and said tip is secured to said shaft by said projection extending into said tip proximal region wall.

9. A stent delivery catheter assembly as recited in claim 8, wherein said projection includes sharp edges and said edges cut into said tip wall.

10. A stent delivery catheter assembly as recited in claim 8, wherein said tip includes an internal recess receiving said projection.

11. A stent delivery catheter assembly as recited in claim 8, wherein said shaft projection includes a ring and said tip includes an internal annular recess receiving said ring projection.

12. A stent delivery catheter assembly as recited in claim 8, wherein said shaft projection includes a longitudinally oriented fin and said tip includes a longitudinally oriented slot through said wall and said assembly has said tip secured to said shaft by said fin extending through said slot.

13. A loaded, self-expanding stent delivery catheter assembly comprising:

a shaft having a distal end, a distal region, and at least one outwardly extending projection in said shaft distal region;

a retractable sheath having a distal region and a distal end disposed co-axially over said shaft distal region such that said sheath distal end is positioned proximally of said shaft distal end;

a self-expanding tubular stent co-axially disposed over said shaft distal region and disposed co-axially within said sheath distal region, such that said stent is radially constrained by said sheath distal region; and a distal tip co-axially disposed over said shaft distal region distally of said sheath distal region, said tip secured to said shaft, wherein said tip has a maximum radial extent greater than the inside diameter of said stent in a constrained state.

14. A catheter assembly as recited in claim 13, wherein said tip has a maximum radial extent greater than the inside diameter of said sleeve distal end.

15. A catheter comprising:

an elongate shaft having a distal region, a distal end, and radially outward projections extending from said shaft distal region; and a distal tip having a body with a lumen therethrough, wherein said distal tip is disposed over said shaft distal region and is secured at least in part to said shaft by said outward projections extending into said tip body.

* * * * *